US005756710A

United States Patent [19]
Stein et al.

[11] Patent Number: 5,756,710
[45] Date of Patent: May 26, 1998

[54] PHOSPHOROTHIOATE OLIGONUCLEOTIDES THAT BIND TO THE V3-LOOP AND USES THEREOF

[75] Inventors: Cy Stein; Seth Lederman; Gregory Sullivan, all of New York, N.Y.

[73] Assignee: The Trustees of Columbia University in City of New York, New York, N.Y.

[21] Appl. No.: 658,616

[22] Filed: Jun. 5, 1996

[51] Int. Cl.$^6$ ................................................. C07H 71/04
[52] U.S. Cl. ................................. 536/24.5; 536/23.1
[58] Field of Search .................. 536/23.1, 24.5; 514/44; 435/6

[56] References Cited

PUBLICATIONS

Stull et al., Antigene, ribozyme, and aptamer nucleic acid drugs: progress and prospects, Pharm. Res., vol. 12(4), pp. 465–483., 1995.

Baum, R.M., "Combinatorial Approaches Provide Fresh Leads for Medicinal Chemistry." C & EN (1994) 20–26 (Exhibit B).

Buckheit, R.W., et al. Potent and Specific Inhibition of HIV Envelope–Mediated Cell Fusion and Virus Binding by G Quartet–Forming Oligonucleotide (ISIS 5320). Aids Research and Human Retroviruses (1994) 10(11): 1497–1506 (Exhibit C).

Feng, Y., HIV–1 Entry Cofactor:Functional cDNA Cloning of a Seven–Transmembrane, G Protein–Coupled Receptor. Science (1996) 272: 872–877 (Exhibit D).

Ojwang, J.O., et al. T30177, an Oligonucleotide Stabilized by an Intramolecular Guanosine Octet, Is a Potent Inhibitor of Laboratory Strains and Clinical Isolates of Human Immunodeficiency Virus Type 1. Antimicrobial Agents And Chemotherapy (1995) 39:(11) 2426–2435 (Exhibit E).

Ojwang, J.O., et al. Inhibition of Human Immunodeficiency Virus Type 1 Activity In Vitro by Oligonucleotides Composed Entirely of Guanosine and Thymidine. Journal of Acquired Immune Deficiency Syndromes (1994) 7: 560–570 (Exhibit F).

Rusche, J.R., et al. Antibodies that inhibit fusion of human immunodeficiency virus–infected cells bind a 24–amino acid sequence of the viral envelope, gp120. Proc. Natl. Acad. Sci. U.S.A. 85: 3198–3202 (1988) (Exhibit G).

Skinner, M.A., et al. Characteristics of a Neutralizing Monoclonal Antibody to the HIV Envelope Glycoprotein. Aids Research and Human Retroviruses 4(3): 187–197 (1988) (Exhibit H).

Stein, C.A., et al. Phosphorothioate Oligodeoxynucleotides Bind to the Third Variable Loop Domain (v3) of Human Immunodeficiency Virus Type 1 gp120. Antisense Research And Development 3: 19–31 (1993) (Exhibit I).

*Primary Examiner*—David Guzo
*Assistant Examiner*—Andrew Wang
*Attorney, Agent, or Firm*—John P. White

[57] ABSTRACT

The present invention provides phosphorothioate oligonucleotide moieties comprising a phosphorothioate oligonucleotide comprising the sequence $G_m X_n G_p$, wherein G is guanosine; X is thymidine, adenosine or cytidine, or a combination thereof; each of m, n and p is independently an integer greater than 2; the phosphorothioate oligonucleotide moiety being capable of binding to a V3 loop of HIV envelope glycoprotein. The invention further provides for a method of inhibiting HIV activity. The invention also provides for a method of inhibiting HIV activity in a subject. The invention further provides for a method of treating an HIV related disorder in a subject. Finally, the invention provides a pharmaceutical composition comprising a phosphorothioate oligonucleotide moiety and a pharmaceutically acceptable carrier.

13 Claims, 8 Drawing Sheets

1 2 3  4 5

1 2 3

1 2 3 4 5

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

GAGGGGAACA GTTCGTCCAT GGC 23

PHOSPHOROTHIOATE OLIGONUCLEOTIDES THAT BIND TO THE V3-LOOP AND USES THEREOF

This invention was made with support under Grant No. RO1CA55713 from the National Institute of Health. Accordingly, the United States Government has certain rights in the invention.

Throughout this application, various publications are referenced by Arabic numerals in brackets. Full citations for these publications may be found at the end of the specification immediately preceding the claims. The disclosures of these publications are in their entirety hereby incorporated by reference into this application to more fully describe the state of the art to which this invention pertains.

BACKGROUND OF THE INVENTION

Phosphorothioate oligodeoxynucleotides belong to a class of polyanions that bind to the third variable domain (V3) of HIV-1 gp120 and inhibit infectivity of a wide variety of HIV-1 isolates. This potent V3 binding of phosphorothioate oligodeoxynucleotides, which is relatively independent of the nucleotide sequence of the oligodeoxynucleotides, decreases with chain length (below 18-mers) and is low for 8-mers. However, recent studies have observed a nucleotide sequence-dependent augmentation of phosphorothioate oligodeoxynucleotide binding to V3 for 8-mers that contain the S-d-$G_4$ motif (e.g. $SdT_2G_4T_2$), and have suggested that formation of quadruple helical tetraplexes (G-tetrads) is associated with the acquisition of V3 binding ability by small phosphorothioate oligodeoxynucleotides. We synthesized a series of -$SdG_4$-containing oligodeoxynucleotides with varying tandem length (including, the 8-mer $SdT_2G_4T_2$, the 12-mer $SdG_4T_4G_4$ and the 28-mer $SdG_4(T_4G_4)_3$) and compared them with phosphorothioate oligodeoxynucleotides (with similar lengths or related sequences) for (1) their inhibition of the binding of mAb 9284, which binds to the N-terminal portion of the V3 loop, (2) the values of $K_c$ when these compounds are used as competitors of the rgp120-binding of an alkylating phosphodiester oligodeoxynucleotide probe, and (3) inhibition of HIV-1 infectivity in a cell-cell transmission model. The presence of S-$dG_4$- motifs and the number of tandem motifs augmented V3-binding and anti-HIV-1 infectivity for small (8- or 12-mer oligodeoxynucleotides) but did not significantly augment the potency of 28-mers. Whereas tetraplex formation of $SdT_2G_4T_2$ may contribute to its V3 binding, the 12-mer $SdG_4T_4G_4$ does not migrate as a tetraplex on non-reducing gels, suggesting that $SdG_4$- motifs may augment anti-HIV activity of multiple mechanisms.

The V3 binding data correlates with the relative abilities of these oligonucleotides to inhibit HIV-1 after cell free or cell associated infection of lymphocytoid H9 cells or of monocytoid U937 cells. In each case, the potency of small oligonucleotides (8–12 mers) was enhanced by -$SdG_4$- motifs, but this augmentation was not observed for longer oligonucleotides (e.g. 28-mers; $SdG_4T_4G_4$ is not as potent a V3 binder as the 28-mers $SdG_4$ $(T_4G_4)_3$ or $SdC28$ ($IC_{50}$=20 nM)). In addition, although the phosphodiester oligonucleotides with -$SdG_4$- motifs may also exist as quadruple helices or as hairpins, they did not bind avidly to V3 and did inhibit mAb 9284 binding. Together, these data indicate that the phosphorothioate backbone is essential for V3 binding and that -$SdG_4$- motifs augment the V3 binding of smaller oligos in the absence of quadruple helix formation. However, the V3 binding of the larger oligonucleotides (e.g. $SdC_{28}$) is not augmented by the presence of this motif.

Polyanionic compounds interact with the V3 loop of gp120 [1–3] and inhibit infectivity of multiple pathogenic strains of HIV-1 [4–9, 28, 29]. Recent data have shown that phosphorothioate oligodeoxynucleotides, which are nuclease resistant, inhibit HIV-1 fusion induced by a number of strains, at least in part by binding to the V3 loop of gp120, in an interaction that depends strongly on the sulfur phosphorothioate backbone, but is relatively independent of the nucleotide sequence of the phosphorothioate oligodeoxynucleotides [10–13]. The ability of homopolymeric phosphorothioate oligodeoxynucleotides to bind in a sequence non-specific manner to the V3 loop decreases with chain length below 18-mers and is low for 8-mers [13]. However, a more recent study, employing $SdT_2G_4T_2$, showed that nucleotide sequence-dependent augmentation of 8-mer phosphorothioate oligodeoxynucleotides binding to the V3 loop of gp120 could be mediated by S-$dG_4$- motifs [14]. Furthermore, $SdT_2G_4T_2$ possesses the ability to inhibit HIV-1 infectivity, albeit with modest potency ($IC_{50}$=1 µM) [30, 14]. The present invention addresses how S-$dG_4$- motifs contribute to augmented V3 binding.

The presence of polydeoxyguanine motifs in 8-mer phosphorothioate oligodeoxynucleotides suggested that secondary structure may be involved in the augmentation of V3-binding [14]. Phosphodiester oligodeoxynucleotides with -$dG_4$- motifs are known to form quadruple helices which are stabilized by guanosine quartet hydrogen bonding (G-tetrads) and metal ions such as $Na^{30}$ or $K^{30}$; structures of this type have been extensively characterized by NMR and X-ray crystallography [15–17]. $SdT_2G_4T_2$ can exist in solution, in fact, as a parallel stranded quadruple helix, and it is in this form that it is the most potent as a V3 binder [14].

In the subject invention, synthetic phosphorothioate oligodeoxynucleotides of defined sequence and length have been utilized to study whether the augmentation of V3-binding which is observed for small oligodeoxynucleotides by S-$dG_4$- motifs occurs for oligodeoxynucleotides with longer sequences as might obtain from a potentiation of G-tetrads formation by intramolecular folding. The presence of four contiguous guanosine residues contributes to the potency of V3 binding and anti-HIV effects for small oligos (8–12-mer phosphorothioate oligodeoxynucleotides), however, the presence of four contiguous guanosine residues does not improve the potency of oligodeoxynucleotides with longer sequences (e.g. 28-mers). The S-$dG_4$- motifs augment V3 binding by at least two mechanisms; whereas the 8-mer $SdT_2G_4T_2$ was shown to form tetraplex structures, the 12-mer $SdG_4T_4G_4$ has augmented potency, independent of frank higher order structures such as quadruple helices.

SUMMARY OF THE INVENTION

The present invention provides a phosphorothioate oligonucleotide moiety comprising a phosphorothioate oligonucleotide comprising the sequence $G_mX_nG_p$, wherein G is guanosine; X is thymidine, adenosine, or cytidine, or a combination thereof; each of m, n and p is independently an integer greater than 2; said phosphorothioate oligonucleotide moiety being capable of binding to a V3 loop of HIV envelope glycoprotein.

The present invention also provides for a method of inhibiting HIV activity comprising contacting HIV with an amount of a phosphorothioate oligonucleotide moiety described herein in an amount effective to inhibit HIV activity.

The present invention further provides for a method of inhibiting HIV activity in a subject which comprises administering to the subject an amount of a phosphorothioate oligonucleotide moiety described herein effective to inhibit HIV activity.

The present invention provides for a method of treating an HIV related disorder in a subject which comprises administering to the subject an amount of a phosphorothioate oligonucleotide moiety described herein effective to treat the HIV related disorder.

The present invention also provides a pharmaceutical composition comprising a phosphorothioate oligonucleotide moiety described herein in an amount effective to bind a V3 loop of HIV envelope glycoprotein and a pharmaceutically acceptable carrier.

Effect of phosphorothioate oligodeoxynucleotides on the binding of mAb 9284 to immobilized rgp120.

Figure 1A:
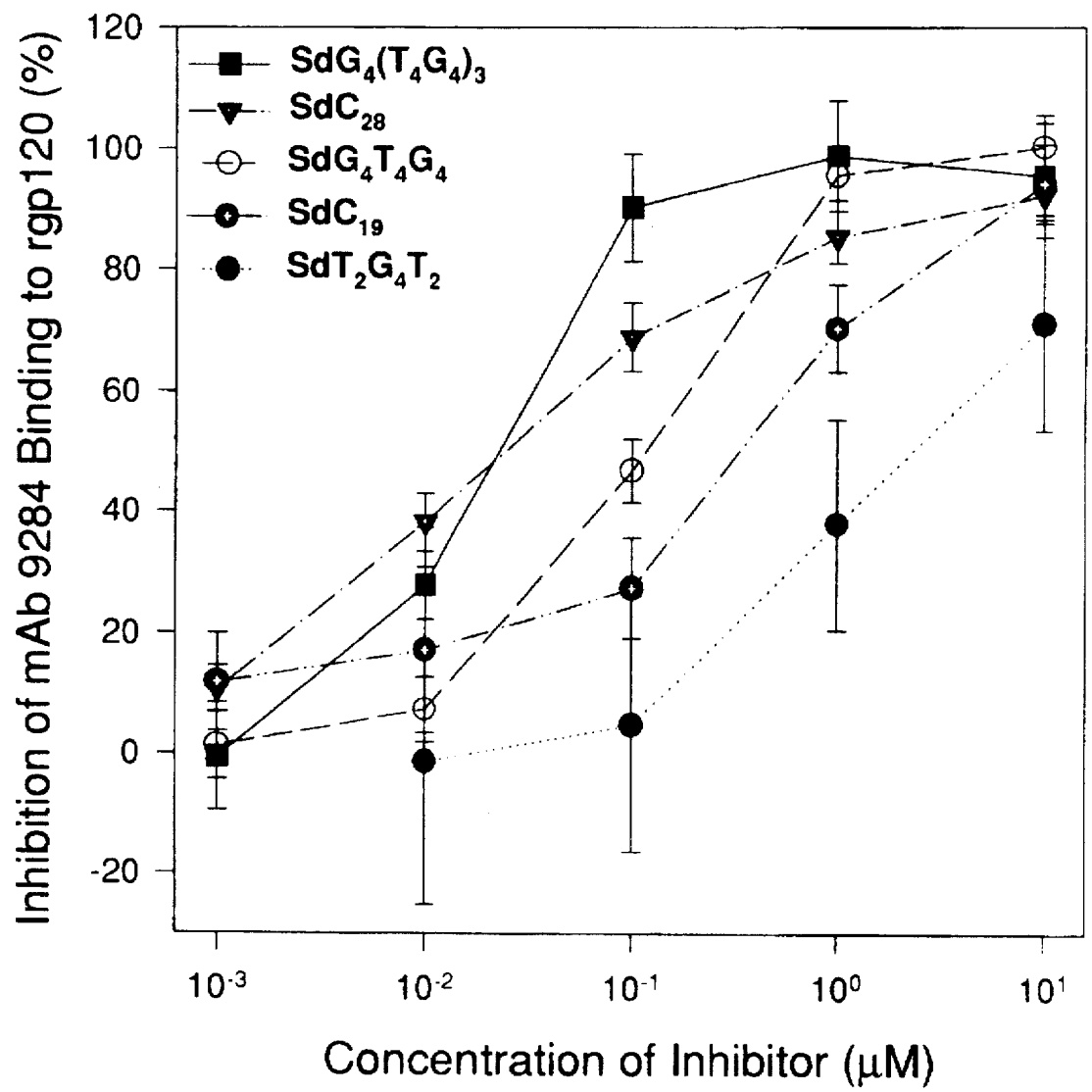
FIGS. 1A–1B.

FIG. 1A: Shown are the effects of the varying concentrations of the indicated phosphorothioate oligodeoxynucleotides on the binding of 9284 to immobilized gp120.

Figure 1B:
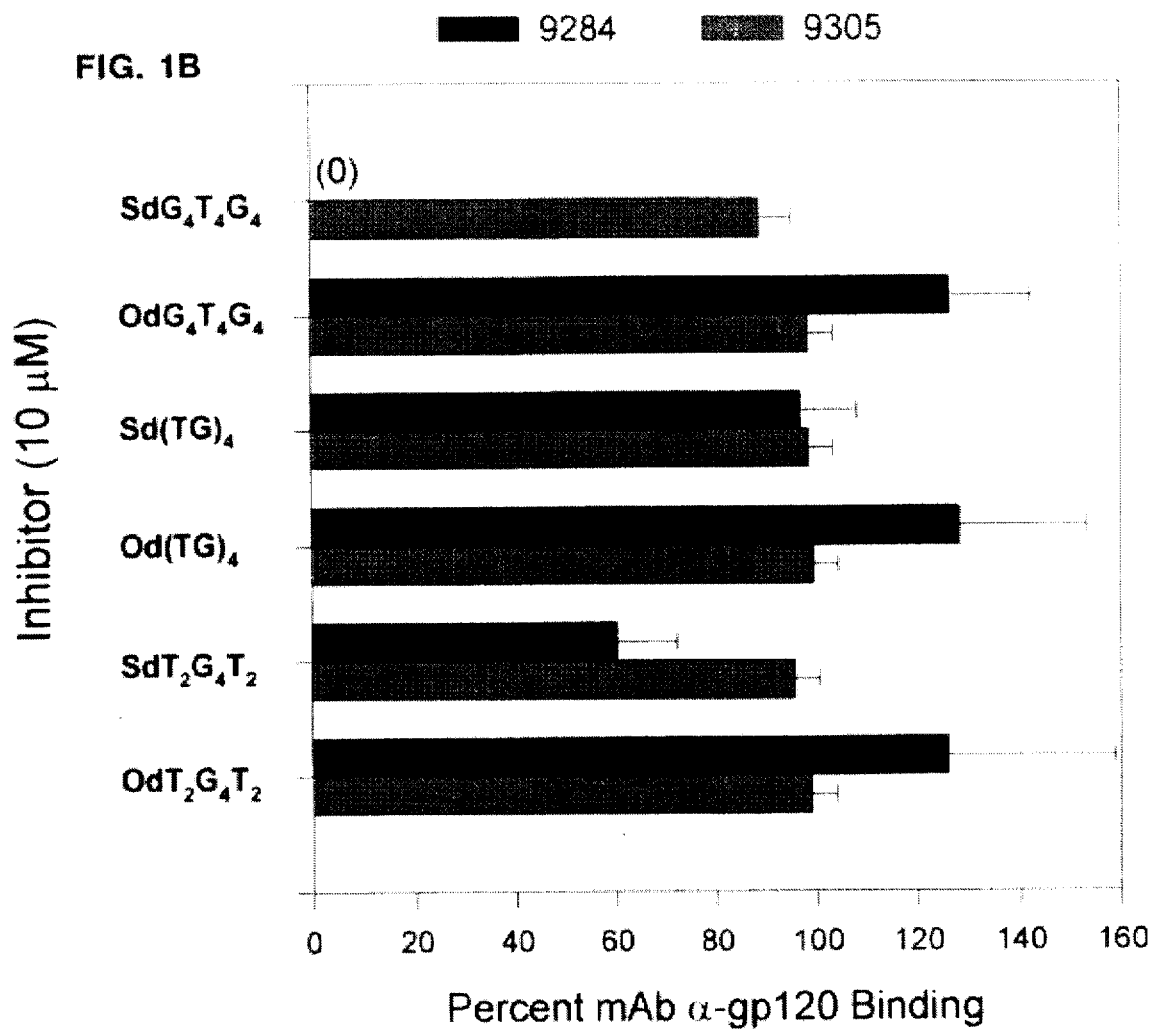

FIG. 1B: Shown are bar graphs representing the binding of anti-V3 gp120 mAbs 9284 or 9305 to immobilized rgp120 in the presence of indicated oligodeoxynucleotides at 10 µM.

FIG. 2:

Solution binding of phosphorothioate oligodeoxynucleotides to rgp120.

Determination of $K_c$ of phosphorothioate and phosphodiester oligodeoxynucleotides competition with the probe oligodeoxynucleotides RC1NH$^{32}$P-OdT$_{18}$ for binding to rgp120. Shown is rgp120 subsequent to treatment with 1 µM probe oligodeoxynucleotides, and subsequent competition for binding. The intensity of the gel bands were quantitated by laser densitometry, and the values of $K_c$ determined by Equation 1. The competitors used were (lanes 1–9, lane 1, OdG$_2$T$_4$G$_2$[2 µM]; lane 2, SdT$_2$G$_4$T$_2$ [1µM]; lane 3, Od(TG)$_4$[2 µM]; lane 4, Sd(TG)$_4$[1 µM]; lane 5, OdG$_4$T$_4$G$_4$ [2 µM]; lane 6, SdG$_4$T$_4$G$_4$ [1 µM]; lane 7, SdT$_{18}$[1 µM]; lane 8, SdC$_{18}$[1 µM]; and lane 9, control (no added competitor).

FIGS. 3A–3D:

Inhibition of HIV-1 infection by oligodeoxynucleotides.

Infection of lymphocytoid H9 and monocytoid U937 cells with an inoculum of chronically HIV-1 (HXB2 or LAI) infected H9 cells was performed as described in methods. One hour after the initiation of infection, cultures were distributed in 96 microwell plates containing different concentrations of inhibitors. Supernatants were harvested and replaced with corresponding media every few days, and batch RT assays were performed after cytopathic effects became apparent. RT activity was quantitated by Betascope and analyzed for inhibitory effects from supernatants harvested on day 7, at which time viral replication in untreated wells had just reached its peak.

Figure 3A:
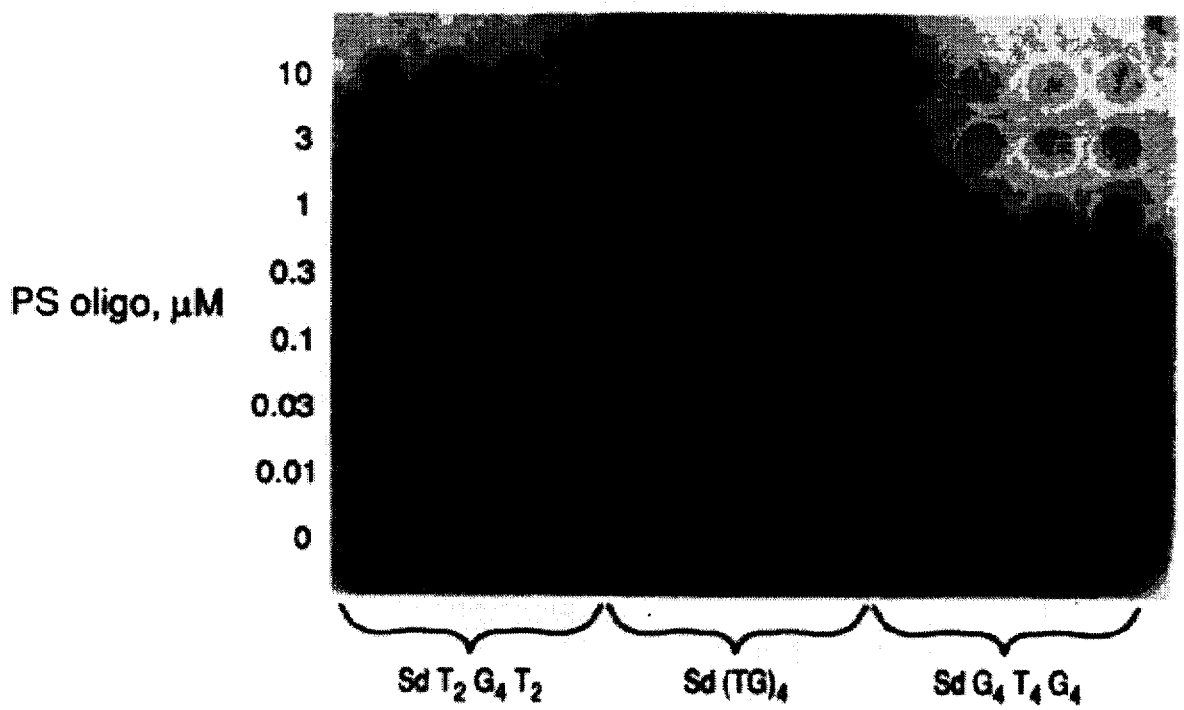

FIG. 3A: Shown are autoradiograms of the RT activity for infected H9 cells in the presence of different inhibitors.

Figure 3B:
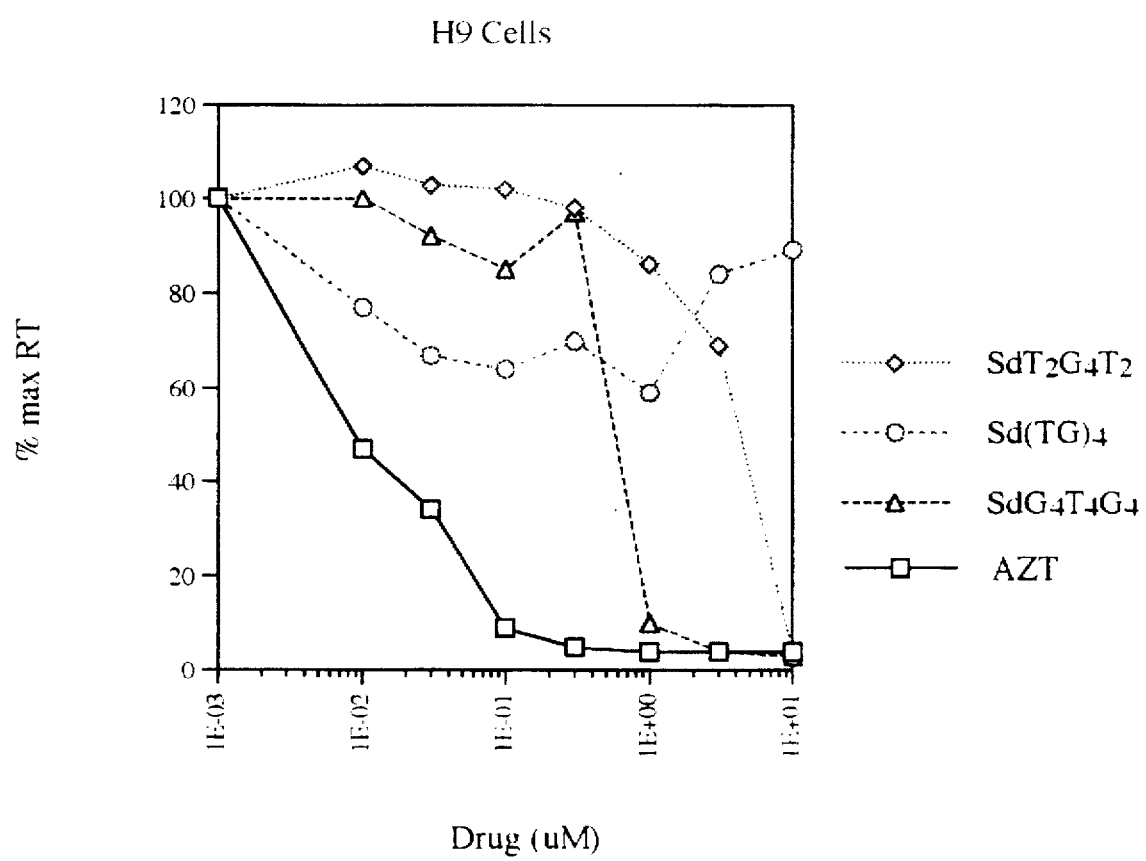

FIG. 3B: Shown is the concentration dependent reduction in maximal RT (obtained in the absence of inhibitors) by each of the indicated compounds for H9 cells. These results are representative of at least three independent experiments for each of the inhibitors, and the graphs were used to derive IC$_{50}$ concentrations for the compounds listed in Table 1, infra.

Figure 3C:
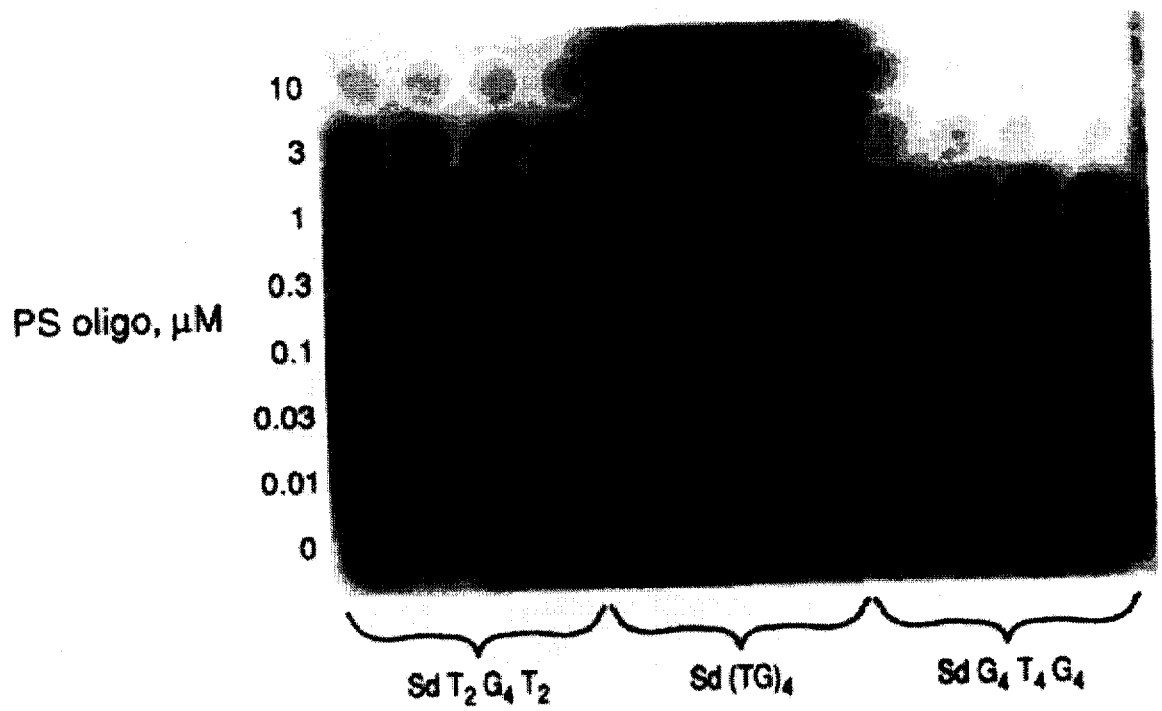

FIG. 3C: Shown are autoradiograms of the RT activity for infected U937 cells in the presence of different inhibitors.

Figure 3D:
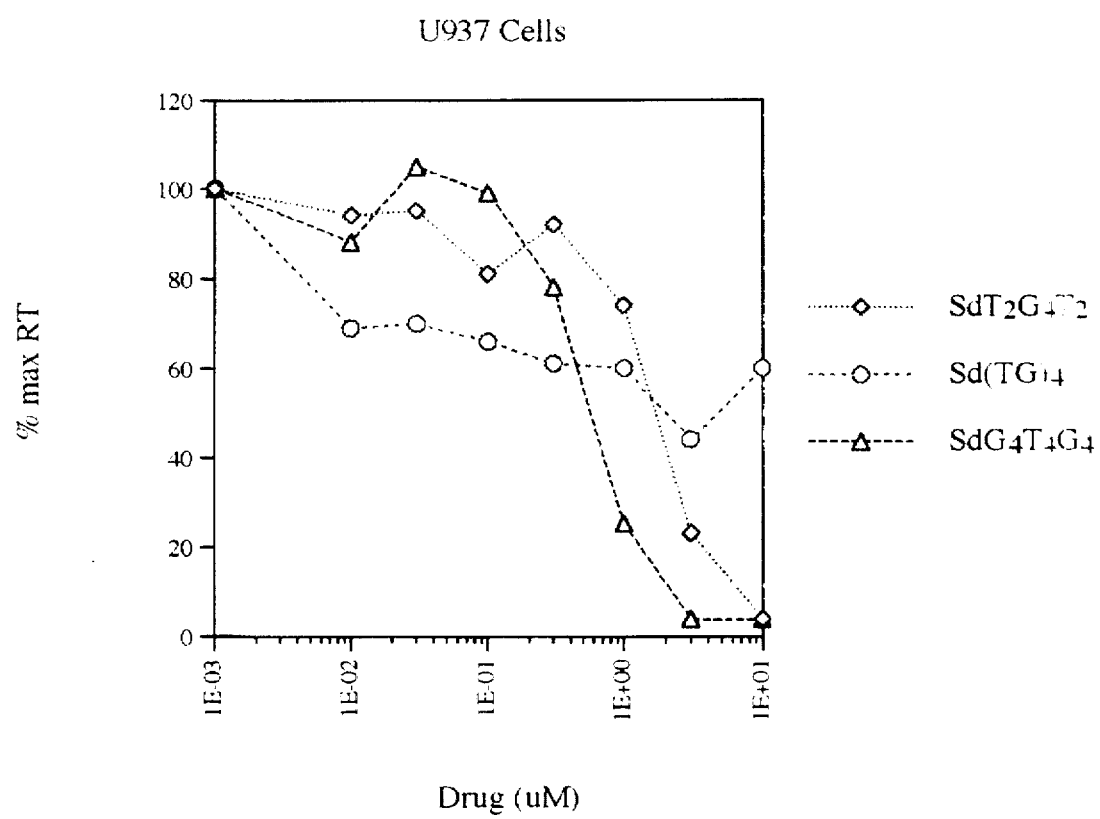

FIG. 3D: Shown is the concentration dependent reduction in maximal RT (obtained in the absence of inhibitors) by each of the indicated compounds for U937 cells. These results are representative of at least three independent experiments for each of the inhibitors, and the graphs were used to derive IC$_{50}$ concentrations for the compounds listed in Table 1, infra.

FIGS. 4A–4C:

Higher order structure of phosphorothioate oligodeoxynucleotides.

Migration of phosphorothioate oligodeoxynucleotides in 20% polyacrylamide gels. Visualization was accomplished by monobromobimane staining, and photography by UV-transillumination.

Figure 4A:
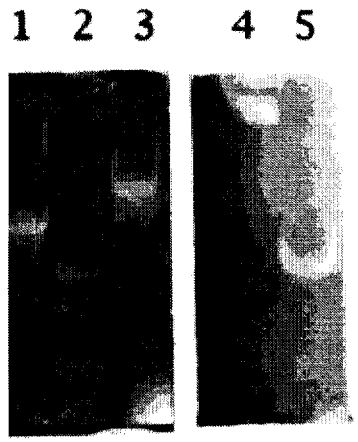

FIG. 4A: Native gel (no added SDS)+140 MM NaCl: Lane 1, SdC$_{28}$; lane 2, SdG$_4$T$_4$G$_4$; lane 3, SdG$_4$(T$_4$G$_4$)$_3$); lane 4, SdG$_6$T$_9$; lane 5, SdC$_{28}$.

Figure 4B:
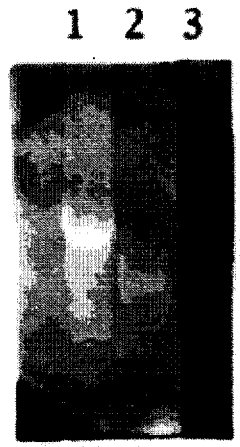

FIG. 4B: Native gel (no added SDS)+140 MM NaCl: lane 1, SdC28; lane 2, SdG$_4$T$_4$G$_4$; lane 3, SdC$_{19}$.

Figure 4C:
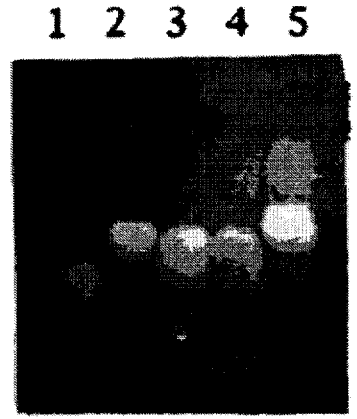

FIG. 4C: 10M urea 20%/phosphiodiesterlyacrylamide gel+pre-boiling in 90% formamide: lane 1, SdG$_6$T$_9$; lane 2, SdC$_{28}$; lane 3, p65 antisense; lane 4, p65 sense; lane 5, SdG$_4$(T$_4$T$_4$)$_3$). [p65 antisense is a 24-mer phosphorothioate oligodeoxynucleotides targeted to the p65 subunit mRNA of the NF-kB nuclear transcriptional regulatory factor. Its sequence is 5'-GAGGGGAACAGTTCGTCCATGGC-3'.]

DETAILED DESCRIPTION OF THE INVENTION

The present invention provides a phophorothioate oligonucleotide moiety comprising a phosphorothioate oligonucleotide comprising the sequence $G_mX_nG_p$; wherein G is guanosine; X is thymidine, adenosine, or cytidine, or a combination thereof; each of m, n and p is independently an integer greater than 2; said phosphorothioate oligonucleotide moiety being capable of binding to a V3 loop of HIV envelope glycoprotein.

Throughout this application, the following standard abbreviations are used to indicate specific nucleotides:

| | | | |
|---|---|---|---|
| C | = Cytidine | A | = Adenosine |
| T | = Thymidine | G | = Guanosine |

Examples of phosphorothioate oligonucleotide moieties include, but are not limited to, a phosphorothioate oligodeoxynucleotide, a phosphorodithioate, a chimeric oligonucleotide, or a phosphorothioate oligonucleotide which is further linked to another chemical moiety.

The term "phosphorothioate oligonucleotide" means an oligonucleotide or oligodeoxynucleotide in which a sulfur atom replaces one or more of the non-bridging oxygen atoms in one or more phosphodiester linkages, i.e. an oligonucleotide or oligodeoxynucleotide having one or more phosphorothiodiester linkages. Each phosphorothiodiester linkage can occur as either an Rp or Sp diastereomer. A bridging oxygen atom is an oxygen atom in a phosphodiester linkage of a nucleic acid which joins phosphorous to a sugar.

One or more of the phosphorothiodiester linkages of the phosphorothioate oligonucleotide moiety may be modified by replacing one or both of the two bridging oxygen atoms of the linkage with analogues such as —NH, —CH$_2$, or —S. Other oxygen analogues known in the art may also be used.

For the purposes of this invention HIV includes, but is not limited to, HIV-1 and HIV-2.

In an embodiment the V3 loop of HIV envelope glycoprotein is as described and depicted in Skinner, et al.

"Characteristics of a Neutralizing Monoclonal Antibody to the HIV Envelope Glycoprotein" [42].

In another embodiment the V3 loop of HIV envelope glycoprotein is the portion of gp120 corresponding to C 303 to C 338 (using the standard numbering of HIV strain IIIb) or comprising C 302 to C337 (using the numbering of HIV strain IIIb by Ratner) [46].

In one embodiment the phosphorothioate oligonucleotide moiety comprises a phosphorothioate oligonucleotide comprising the sequence $G_mX_nG_p$, wherein X is adenosine or thymidine.

In another embodiment the phosphorothioate oligonucleotide moiety comprises a phosphorothioate oligonucleotide comprising the sequence $G_mX_nG_p$, wherein each of m, n and p is 3 to 10 inclusive.

In another embodiment the phosphorothioate oligonucleotide moiety comprises an oligonucleotide comprising the sequence $G_mX_nG_p$ wherein each of m, n and p is 4 and X is thymidine.

The present invention provides that X may be thymidine, adenosine or cytidine, or a combination thereof. Accordingly, X may be any combination of adenosine, thymidine or cytidine residues, provided that the total number of adenosine, thymidine or cytidine residues present in the phosphorothioate oligonucleotide is greater than 2.

In another embodiment the phosophorothioate oligonucleotide of the phosphorothioate oligonucleotide moiety has a length of from about 8 to about 100 nucleotide residues.

A phosphorothioate oligonucleotide may be stereo regular, stereo non-regular or stereo random. A stereo regular phosphorothioate oligonucleotide is a phosphorothioate oligonucleotide in which all the phosphodiester linkages or phosphorothiodiester linkages polarize light in the same direction. Each phosphorous in each linkage may be either an Sp or Rp diastereomer. Phosphorothioate oligonucleotides which are created in an automated synthesizer are stereo random which means that each phosphorous atom in the phosphorothioate oligonucleotide has a 50% chance of being either an Sp or an Rp diastereomer.

In a further embodiment, the phosophorothioate oligonucleotide moiety comprises a phosphorothioate oligonucleotide linked to a chemical moiety, such as a cholesteryl moiety, an intercalating agent, a cross-linker, an artificial endonuclease, a lipophilic carrier, a peptide conjugate, or a combination thereof.

In another embodiment, the phosphorothioate oligonucleotide moiety comprises a phosphorothioate oligonucleotide conjugated to a sulfated carbohydrate, a carbohydrate, or a glycan.

The present invention further provides that one or both ends of the phosphorothioate oligonucleotide of the phosphorothioate oligonucleotide moiety may be linked with the following chemical moieties: intercalating agents, such as acridine derivatives; cross-linkers, such as psoralen derivatives, azidophenacyl, proflavin, and azidoproflavin; artificial endonucleases, which comprise those conjugates whose nuclease component is able to cleave DNA specifically and nonspecifically, and acquires a specificity by covalent linkage to the oligonucleotide portion, such as metal complexes EDTA-Fe (II), o-phenanthroline-Cu(I), and porphyrin-Fe(II); and lipophilic carriers or peptide conjugates, such as long chain alcohols , phosphate esters, amino or mercapto groups, dyes or nonradioactive markers and polylysine or other polyamines.

Furthermore, one or both ends of the phosphorothioate oligonucleotide of the phosphorothioate oligonucleotide moiety may be linked with the following chemical moieties: intercalating agents, such as 2-methoxy-6-chloroacridine, methylphosphonates, methylesters, and aminoalkyls; alkylating oligonucleotides, such as acetyl; artificial endonucleases, such as amino-1-hexanolstaphylococcal nuclease, and alkaline phosphatase; peptide conjugates, such as polylysine; and terminal transferases.

Furthermore, the phosphorothioate oligonucleotide of the phosphorothioate oligonucleotide moiety may be conjugated to a carbohydrate, sulfated carbohydrate, or glycan. Such conjugates may be synthesized so as to introduce a desired specificity into the phosphorothioate oligonucleotide moiety.

In addition, the phosphorothioate oligonucleotide of the phosphorothioate oligonucleotide moiety may be combined with a cationic lipid. Examples of cationic lipids include, but are not limited to, lipofectin, dotma, and dogs.

The phosphorothioate oligonucleotide of the phosphorothioate oligonucleotide moiety may have one or more of its sugars modified or replaced so as to be ribose, glucose, sucrose, or galactose, or any other sugar. Alternatively, the phosphorothioate oligonucleotide may have one or more of its sugars substituted or modified in its 2' position, i.e. 2'allyl or 2'-O-allyl. An example of a 2'-O-allyl sugar is a 2'-O-methylribonucleotide. Further, the phosphorothioate oligonucleotide may have one or more of its sugars substituted or modified to form an α-anomeric sugar.

Furthermore, the phosphorothioate oligonucleotide of the phosphorothioate oligonucleotide moiety may have one or more of its nucleotide bases substituted or modified. Apart from the bases of adenine, guanine, cytosine, and thymine, other natural bases such as inosine, deoxyinosine, and hypoxanthine are acceptable in the phosphorothioate oligonucleotide moiety useful in the subject invention. In addition, isosteric purine 2'deoxy-furanoside analogues, 2'-deoxynebularine or 2'deoxyxanthosine, or other purine and pyrimidine analogues may also be used. The guanosine bases comprising the phosphorothioate oligonucleotide sequence may not be substituted or modified.

In another embodiment the phosphorothioate oligonucleotide has a length of from about 8 to about 100 nucleotide residues.

The present invention also provides a method of inhibiting HIV activity which comprises contacting HIV with an amount of a phosphorothioate oligonucleotide moiety described herein in an amount effective to inhibit HIV activity.

As used herein, the phrase "an amount effective to inhibit HIV activity" means that amount which is effective to inhibit the HIV activity of HIV in a cell. The $IC_{50}$ values of the phosphorothioate oligonucleotides of the present invention are approximately 10 nanomolar. Accordingly, the preferred serum concentration of the phosphorothioate oligonucleotides of the present invention is from about 10 micromolar to about 1 nanomolar, preferably about 1 micromolar. An effective amount will vary with the particular compound in use, the strength of the preparation, the mode of administration, and the advancement of the disease condition. Additional factors depending on the particular subject being treated that will result in a need to adjust dosages, include subject age, weight, gender, diet and time of administration.

The present invention further provides for a method of treating an HIV related disorder in a subject which comprises administering to the subject an amount of the phosphorothioate oligonucleotide moiety described herein effective to treat the HIV related disorder.

Examples of HIV related disorders include, but are not limited to, AIDS, immunodeficiency, central nervous system disease, HIV encephalopathy, neuropathy, pneumocystis, Kaposi's sarcoma, carinii pneumonia, non-Hodgkin's lymphoma, and Hodgkin's lymphoma. Other HIV related disorders are known in the art, and any of these disorders may be treated according to the invented method.

Throughout this application the use of the present invention has been described in association with HIV. As stated previously, the invention may be used to inhibit HIV-1 and/or HIV-2 activity. The invention may also be used to inhibit activity of any virus that uses a cationic moiety to mediate fusion with the host membrane. This invention further provides a phosphorothioate oligonucleotide moiety comprising a phosphorothioate oligonucleotide having the sequence $G_mX_nG_p$, wherein G is guanosine; X is thymidine, adenosine or cytidine, or a combination thereof; each of m, n and p is independently an integer greater than 2; said phosphorothioate oligonucleotide moiety being capable of binding to a surface protein of a virus that uses a cationic moiety to mediate fusion with the host membrane.

The present invention may be used to treat an HIV infection in which the infection was acquired by transfusion with blood or blood products, sexual contact, a laboratory accident, a needle stick injury (seroconversion), trauma, intravenous drug use, transfusion of organs or organ products, or any other route of infection. The HIV infection may have been transmitted via maternal-fetal transmission.

The present invention may be used when HIV infection has occurred or when there is a chance that HIV infection may have occurred or in instances in which HIV infection may occur (ie. needle stick injury). Thus, "inhibiting HIV activity in a subject" according to the present invention encompasses both prevention and treatment of HIV.

The present invention also provides a pharmaceutical composition comprising a phosphorothioate oligonucleotide moiety described herein in an amount effective to bind a V3 loop of HIV envelope glycoprotein and a pharmaceutically acceptable carrier.

As used herein, the phrase "an amount effective to bind to a V3 loop of HIV envelope glycoprotein" means that amount which is effective to bind to a V3 loop of HIV envelope glycoprotein. An effective amount will vary with the particular compound in use, the strength of the preparation, the mode of administration, and the advancement of the disease condition. Additional factors depending on the particular subject being treated that will result in a need to adjust dosages, include subject age, weight, gender, diet and time of administration.

For the purposes of this invention examples of "HIV activity" include, but are not limited to, replication, infectivity, cell-cell fusion (syncytia), the formation of multinucleated giant cells and the formation of heterokaryons. Means of measuring HIV infectivity and/or replication include but are not limited to, measuring p24 production, measuring reverse transcriptase activity, and/or measuring viral load.

In any of the methods disclosed herein the phosphorothioate oligonucleotide moiety may be administered to the subject in a pharmaceutical composition via any known mode of administration.

Such means of administration are well known to those skilled in the art and include, but are not limited to, topical administration, parenteral administration, oral administration, or intraperitoneal, intravenous, intrathecal, intratracheal, intramuscular, or subcutaneous injection. Administration of the phosphorothioate oligonucleotide moiety may be effected continuously or intermittently. Furthermore, the phosphorothioate oligonucleotide may be administered by itself or in combination with cationic lipids or other carriers.

A pharmaceutical composition comprising a phosphorothioate oligonucleotide moiety described herein may include any of the known pharmaceutical carriers. Examples of suitable pharmaceutical carriers include any of the standard pharmaceutically accepted carriers known to those of ordinary skill in the art. Examples of such pharmaceutical carriers include, but are not limited to, phosphate buffered saline solution, water, emulsions such as oil/water emulsions or a triglyceride emulsion, various types of wetting agents, tablets, coated tablets and capsules. A suitable pharmaceutically acceptable carrier may be selected taking into account the chosen mode of administration.

An effective amount of a pharmaceutical composition comprising a phosphorothioate oligonucleotide moiety is that amount which is effective to bring about the desired effect in the subject. Accordingly, an effective amount will depend on various factors known to those of ordinary skill in the art. Such factors include, but are not limited to, the size of the subject and the degree to which the disease from which the subject suffers has progressed. The effective amount will also depend on whether the phosphorothioate oligonucleotide moiety is going to be administered to the subject in a single dosage or periodically over a stretch of time.

The phosphorothioate oligonucleotide moieties of the present invention may be combined with other medicaments commonly used to treat subjects suffering from HIV related disorders. Examples of such medicaments include, but are not limited to, agents that inhibit CD4-gp120 interactions, including antibodies to CD4 or gp120, soluble CD4, and peptides from CD4 or gp120 that inhibit gp120 activity; protease inhibitors such as indinavir sulfate; reverse transcriptase inhibitors such as zidovudine, azidothymidine, lamivudine or a combination of reverse transcriptase inhibitors; and therapeutic HIV vaccines.

This invention will be better understood from the Examples in the "Experimental Details" Section which follows. However, one skilled in the art will readily appreciate that the specific methods and results discussed therein are merely illustrative of, and are not intended to, nor should they be construed to, limit the invention as described more fully in the claims which follow thereafter.

EXPERIMENTAL DETAILS

Materials and Methods

Reagents:

The rgp120 used was purchased from American BioTechnologies (Cambridge, MASS.). The murine IgG1 anti-gp120 mAbs, NEA 9284 [18], NEA 9301 and NEA 9305 (also known as mAb 0.5 β[20]) were purchased (Dupont, Boston, Mass.). AZT was obtained from Burroughs Welcome Research Laboratories.

Oligodeoxynucleotides:

Oligodeoxynucleotides were synthesized on a DNA Synthesizer by the manufacturer's suggested procedures (ABI 380B, Applied Biosystems, Foster City, Calif.). After synthesis, the oligodeoxynucleotides were deblocked in aqueous ammonia at 60° C. for 8 hrs and HPLC purified over a PRP-1 column in a gradient of 0.1M triethylammonium bicarbonate/acetonitrile as described previously [19]. After detritylation in 3% acetic acid and lyophilization, the oligodeoxynucleotides were dissolved in water, and precipitated with a 10-fold excess volume of 2% lithium perchlorate/acetone, washed with acetone, and dried in vacuo. The oligodeoxynucleotides were then reprecipitated as the sodium salt from aqueous ethanol.

Synthesis of the probe, alkylating oligodeoxynucleotide RCl$^{32}$PNH-OdT18

Approximately 6 OD units of OdT$_{18}$ were 5' labeled with $^{32}$P-phosphate by reaction with 5'-polynucleotide kinase [31]. Excess ATP was separated from reaction product by Sephadex G25 chromatography in 0.1M lithium perchlorate. The oligodeoxynucleotide was then precipitated by addition of 2% LiClO$_4$/acetone, and dissolved in water at a concentration of 200 OD units/µL. The oligodeoxynucleotide was then precipitated by addition of 7 µL of an 8% aqueous solution of cetyltrimethylammonium bromide solution and dried. To this was added 6 µg of p-(benzylamino)-N-2-chloroethyl-N-methylamine (ClRNH$_2$) in 20 µL of dimethylformamide, followed by 8 µg of dipyridyl disulfide and 9.5 µg of triphenylphosphine. 50 µL of methanol were added, and the oligodeoxynucleotide was precipitated by addition of 2% lithium perchlorate/acetone. The product (ClRNH$^{32}$P-OdT$_{18}$) was redissolved in water, precipitated again as above, and stored in water at −80°C.

Determination of K$_c$ of oligodeoxynucleotides competing for ClRNH$^{32}$P-OdT$_{18}$ binding to rgp120

The value of K$_d$ (approximately 1 µM) has been previously determined from the concentration dependence of rgp120 binding and alkylation by ClRNH$^{32}$P-OdT$_{18}$ [13]. To 10 µL of a solution of 0.025 mg/mL rgp120 (in Tris HCl, 0.1M, pH 7.5) were added ClRNH$^{32}$P-OdT$_{18}$ (in 5 µL Tris HCl, 0.1M, pH 7.5) to give the final concentration of 2 µM. After incubation of the mixture at 37° C. for 1 hour, 7.5 µL of a buffer containing 50% glycerol, 0.1M dithiothreitol, 2% SDS and 0.001% bromophenol blue was added to each sample, and polyacrylamide gel electrophoresis performed. The gel was dried and allowed to expose Kodak X-ray film for the appropriate times. For quantitation of rgp120-bound oligodeoxynucleotides, the developed film was overlayed on the gel, and the gel regions were excised and counted in a β counter. To determine competition constants (K$_c$) for phosphorothioate oligodeoxynucleotide competitors of ClRNH$^{32}$P-OdT$_{18}$ binding to rgp120, the appropriate concentration of competitor (1 or 2 AM) was added to the reaction mixture.

The value of Kc could be calculated from Equation 1 [24]

$$K_c = K_d \times [C/L_1 \times [1/R_o/R_c) - 1]$$  Equation 1 where K$_c$ and K$_d$ are as previously described C=[competitor], L$_1$=[ClNH$^{32}$P-OdT$_{18}$] (=2 µM), and R$_o$/R$_c$=the number of bound counts in the absence and presence of competitor, respectively. The determination of K$_c$ via Equation 1 is a variation of the method of Cheng and Prusoff [32]. Equation 1 is valid only if the alkylating oligodeoxynucleotide or competitor are used at saturating concentrations, if not, the actual value of K$_c$ may be lower than the measured value.

ELISA binding assays

The adherence of rgp120 to the U bottoms of untreated polystyrene plates (Corning, Corning N.Y.) was achieved by incubation of 50 µL of a rgp120 solution (1 µg/mL) in phosphate buffered saline (PBS) for 2 h at room temperature. Control wells were treated with PBS without added protein. Wells were washed three times with PBS containing 0.05% Tween-20 (PBS-Tween) followed by blocking with 0.15 mL of 1% BSA at 4° C. overnight. The wells were then washed three times in PBS-Tween before 50 µL of solutions containing the phosphorothioate or phosphodiester oligodeoxynucleotides, at the given concentrations, plus the mAb were added to control and protein-coated wells and allowed to react for 30 min at room temperature. Control solutions contained 1% BSA in water or in PBS. To detect bound ligands, 50 µL of the anti-gp120 mAb in 1% BSA were added to the wells and reacted for 90 min at 20° C. The wells were washed four times before the addition of 50 µL of 1:1000 affinity purified goat anti-mouse IgG conjugated to alkaline phosphatase (Bio-rad Laboratories, Richmond, Calif.) in 1% BSA. After 60 min, wells were washed four times before addition of 50 µL substrate solution (p-nitrophenylphosphate). The enzyme reaction was allowed to progress at 20° C. for 20–60 min before absorption at 405 nm was measured in an ELISA plate analyzer (VMAX, Molecular Devices Corporation, Palo Alto, Calif.). Assays were performed in triplicate. Standard deviations (SD) were obtained by the STDEV formula (Excel, Microsoft, Redmond, Wash.). The standard deviations of the subtracted means (A−B) obtained from the formula S.D. (A−B)=SQR (SD(A)$^2$=SD(B)$^2$).

Viral Replication Assays

Antiviral effects of oligodeoxynucleotides were evaluated in tissue culture. H9 cells chronically infected with HIV-1 LAI strain were maintained as previously described [33]. Cells and supernatant were used to transmit virus to fresh lymphocytoid H9 cells or monocytoid U937 cells. 5×10$^6$ recipient cells in 1 ml of RPMI 10% FCS were incubated with 1 ml of a dilution of chronically infected cells containing 10$^4$ viable cells (1:100 dilution), with gentle mixing. After 2 hrs at 37° C., the cells were diluted to 15 ml of RPMI FCS and 100 µl samples (containing 3×10$^4$ cells) were added to wells of a 96 well plate containing an equal volume of media plus oligodeoxynucleotides at 2× final concentration. Supernatants were harvested and frozen twice per week, and at each time half the volume was replaced with fresh drug containing medium. After 14 days, supernatants were quantitatively assayed for RT transcriptase (RT) activity as described [33]. RT values from the day in which peak RT activity was reached in the absence of drug were used to calculate the IC$_{50}$ values of the oligodeoxynucleotides and AZT.

Results

Comparison of the ability of phosphorothioate and phosphodiester oligodeoxynucleotides to inhibit the binding of mAb 9284 to rgp120

The effect of the S-dG$_4$-motif on phosphorothioate oligodeoxynucleotides binding to gp120 was studied by measuring the effect of these compounds on the binding of the two anti-gp120 V3 mAbs, 9284 and 9305, to rgp120 in a solid phase ELISA assay. It has previously been shown that SdC$_{28}$ (but not OdC$_{28}$) specifically inhibits the gp120 binding of mAb 9284 [13]. The 9284 mAb recognizes the N-terminal portion of the V3 loop of rgp120 [18]. However, SdC$_{28}$ does not inhibit binding of mAb 9305 [13], which recognizes a contiguous and overlapping site C-terminal to 9284 on the V3-loop [18, 20]. Because SdT$_2$G$_4$T$_2$ has recently been shown to bind V3 [14], the effect of SdT$_2$G$_4$T$_2$ on mAb 9284 binding was studied first. Similar to the published reports of its effect on the binding of anti-V3 antiserum [14], SdT$_2$G$_4$T$_2$ inhibits mAb 9284 binding to the V3 loop (IC$_{50}$=4.2 µM) (FIG. 1A). However, even at 10 µM (at which SdT$_2$G$_4$T$_2$ inhibits 70% of 9284 binding), neither OdT$_2$G$_4$T$_2$ nor Sd(TG)$_4$ inhibit mAb 9284 binding (FIG.

1B). These data are consistent with published reports that both the phosphorothioate backbone and the presence of an -SdG$_4$- motif are required for V3 loop binding (FIG. 1B) [14]. Moreover, in addition to confirming the V3-specific binding of SdT$_2$G$_4$T$_2$, the finding that SdT$_2$G$_4$T$_2$ does not inhibit mAb 9305 binding to the V3 loop (FIG. 1B) extends the understanding of its binding domain by mapping binding to the N-terminal half of the V3 loop. This behavior is similar to that of larger SdC-homopolymers, such as SdC$_{28}$ as well as sulfated polysaccharides [3, 13]. However, although, the -SdG$_4$- motif confers on SdT$_2$G$_4$T$_2$ a sequence-dependent augmented potency for V3-binding relative to oligodeoxynucleotides of comparable size and base composition, the binding of SdT$_2$G$_4$T$_2$ to gp120 V3 is substantially weaker than that of SdC$_{28}$ (FIG. 1A, Table 1) [13].

To address the possibility that tandem S-dG$_4$- motifs may further facilitate binding to the V3 loop of gp120, the effect of SdG$_4$T$_4$G$_4$ on mAb anti-gp120 V3 binding to rgp120 was studied. Similar to other phosphorothioate oligodeoxynucleotides, SdG$_4$T$_4$G$_4$ inhibits the binding of the anti-gp120 V3 mAb 9284 but not mAb 9305 (FIG. 1A). In addition, the corresponding phosphodiester oligodeoxynucleotide, OdG$_4$T$_4$G$_4$, does not inhibit mAb 9284 binding at the concentrations tested (10 μM, FIG. 1B). SdG$_4$T$_4$G$_4$ blocks mAb 9284 binding to the V3 loop with IC$_{50}$=0.16 μM; thus, its activity is higher than the 8-mer SdT$_2$G$_4$T$_2$ (IC$_{50}$=4.2 μM (FIG. 1A, Table 1). Its activity is slightly lower than SdC$_{28}$ (IC$_{50}$=0.044 μM), which is an oligodeoxynucleotide of substantially longer length (28-mer vs 12-mer) (FIG. 1A, Table 1). The corresponding value of IC$_{50}$ for SdT$_{19}$ is 0.570 μM (FIG. 1A). These data suggested that the tandem -S-dG$_4$- repeats in SdG$_4$T$_4$G$_4$ increase the ability of the phosphorothioate oligodeoxynucleotides to bind to the V3 loop of gp120.

The next series of experiments addressed whether an additional tandem repeat, provided by appending -SdT$_4$G$_4$T$_4$G$_4$- to SdG$_4$T$_4$G$_4$, would confer increased V3 binding on the new oligodeoxynucleotide, SdG$_4$(T$_4$G$_4$)$_3$. SdG$_4$(T$_4$G$_4$)$_3$ binds to rgp120 and inhibits mAb 9284 binding with IC$_{50}$=0.042 μM (FIG. 1A, Table 1). It is thus more potent on a molar basis than SdG$_4$T$_4$G$_4$, but its almost identical in potency to SdC$_{28}$, which does not contain S-dG$_4$- motifs.

Determination of the value of K$_c$ for competition by phosphorothioate oligodeoxynucleotides of the binding of RCLNH$^{32}$P-OdT18 to rgp120

Figure 2:
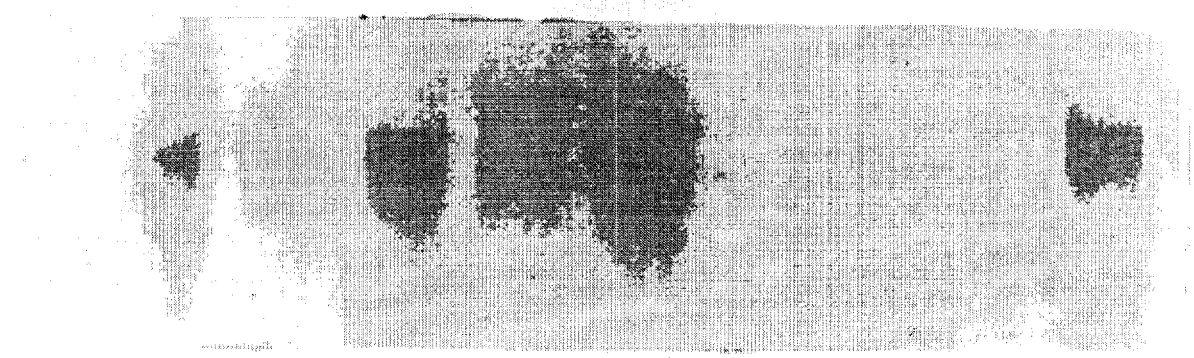

The nature of the interaction S-dG$_4$- motif containing oligodeoxynucleotides with gp120 was probed by measuring the K$_c$ of competition for a probe, alkylating phosphodiester oligodeoxynucleotide. An 18-mer phosphodiester homopolymer of thymidine which has been 5'-end modified with an alkylating moiety and $^{32}$p was employed to produce the probe RClNH$^{32}$P-OdT$_{18}$. (FIG. 2). The use of this probe permits the evaluation of the ability of other phosphodiester and phosphorothioate oligodeoxynucleotides to inhibit probe binding and subsequent alkylation of gp120 by the radiolabeled probe oligodeoxynucleotide.

Subsequent to alkylation, the $^{32}$P-labeled alkylating oligodeoxynucleotide-protein complex was visualized autoradiographically after denaturing gel electrophoresis [13].

Phosphorothioate and phosphodiester oligodeoxynucleotides were studied as competitors of probe oligodeoxynucleotides binding to rgp120. As shown in FIG. 2, in the presence of a competitor of probe oligodeoxynucleotide binding, the intensity of the gel band, which represents rgp120 modified by the probe oligodeoxynucleotide decreased (FIG. 2, compare lane 9 (control) with lanes 6 (SdG$_4$T$_4$G$_4$), lane 7 (SdT$_{18}$) and lane 8 (SdC$_{18}$)). In the presence of phosphorothioate oligodeoxynucleotides, CIRNH$^{32}$P-OdT$^{18}$ binding to rgp120 was competed to a greater extent than in the presence of phosphodiester oligodeoxynucleotides (FIG. 2, compare lanes 6(SdG$_4$T$_4$G$_4$) and 2(SdT$_2$G$_4$T$_2$), with lane 5(OdG$_4$T$_4$G$_4$)

Determination of the approximate values of K$_c$ of phosphorothioate oligodeoxynucleotide binding to rgp120 was accomplished by use of Equation 1; these are shown in Table 1. An error of 15% is assumed due to the presence of non-specific background on the X-ray film. The value of K$_c$ for SdC$_{18}$ as determined by Equation 1 is 0.020 μM. The value of K$_c$ for SdC$_{18}$, as determined via the Cheng-Prusoff equation [13] is 0.022 μM. Thus, under the conditions used in these experiments, the two methods of determination of K$_c$ give approximately equivalent results.

It is apparent that there is a substantial diminution in the value of K$_c$ for SdT$_2$G$_4$G$_4$ relative to SdT$_2$G$_4$T$_2$. Further, the value of K$_c$ for the 12-mer SdG$_4$T$_4$G$_4$ is similar for that determined for SdC$_{28}$ or SdG$_4$(T$_4$G$_4$)$_3$. In each case, the magnitude of K$_c$ for each compound correlates with their ability to block mAb 9284 binding to the V3 loop of rgp120 in the solid phase ELISA binding assay (Table 1).

Effect of phosphorothioate and phosphodiester oligodeoxynucleotides on HIV-1 infectivity To determine if the V3-loop binding correlates with an antiviral effect on HIV-1 infection, the ability of these oligodeoxynucleotides to limit HIV-1 infection in both the lymphocytoid cell line, H9 (FIG. 3A and 3B) and the monocytoid cell line, U937, (FIG. 3C and 3D), was examined. Infection of these cell lines was initiated by addition of a small inoculum of chronically infected H9 cells, followed by culture in the presence of different concentrations of oligodeoxynucleotides. Interference with viral replication in this assay is a stringent test of the ability of a compound to affect new rounds of both cell free and cell-cell viral infection. Cell viability in the absence of infection was not affected by oligodeoxynucleotides at the concentrations used (data not shown). FIGS. 3A and 3B show that SdT$_2$G$_4$T$_2$ inhibits HIV-1 infectivity in H9 cells with IC$_{50}$ of 4.0 μM, which is similar to the results of published studies [14]. In contrast, SdG$_4$T$_4$G$_4$ inhibits HIV-1 more potently, with IC$_{50}$ of 0.55 μM (FIGS. 3A and 3B). Similarly, SdT$_2$G$_4$T$_2$ inhibits HIV-1 infectivity in U937 cells with IC$_{50}$ of 1.8 μM, whereas, SdG$_4$T$_4$G$_4$ inhibits HIV-1 infection in U937 cells more potently (3–9 fold), with IC$_{50}$ of 0.55 μM (FIGS. 3C and 3D). These effects correlate with the increased potency of SdG$_4$T$_4$G$_4$ for binding rgp120 in both the solid phase and solution competition assays (FIGS. 1A, 1B and 2, Table 1). Furthermore, SdG$_4$(T$_4$G$_4$)$_3$ inhibits HIV-1 infection in H9 cells with IC$_{50}$ of 0.01 μM, which is more potent (3–9 fold) than the smaller oligodeoxynucleotides, but not significantly different from SdC$_{28}$(IC$_{50}$=0.01 μM) (Table 1). Taken together, these data suggest a relationship between the affinity of gp120 V3-loop binding and the ability of the oligodoexynucleotides to inhibit the infectivity of HIV-1 in tissue culture. Therefore, similar to the in vitro binding and inhibition of HIV-1 infectivity, the augmented potency of S-dG$_4$-containing oligodoexynucleotides is particularly evident for the 8-mer SdT$_2$G$_4$T$_2$ and the 12-mer SdG$_4$T$_4$G$_4$ compounds, but is lost for longer sequences (e.g. 28-mers).

Solution structure of phosphorothioate oligodeoxynucleotides

The next series of experiments addressed the state of the phosphorothioate oligodoexynucleotides in solution. The solution states of these oligodeoxynucleotides were studied by examining their migration in non-SDS containing polyacrylamide gels after staining with 0.25 mM monobromobimane (Calbiochem, San Diego, CALIF.) and visualization by fluorescent transillumination. As a positive control for tetraplex formation $SdG_6T_9$ which exists in solution as quadruple helix (similar to $SdT_2G_4T_2$) was studied. Although $SdG_6T_9$ is a 15-mer (FIG. 2, lane 4) it migrates on a native polyacrylamide gel much slower than $SdC_{28}$ (FIG. 2, lane 5), however, treatment of $SdG_6T_9$ with 10M urea/formamide dissociates it into rapidly mobile monomers (FIG. 2, lane 2).

Surprisingly, $SdG_4T_4G_4$ that displayed potent V3 binding relative to other 12-mers, migrates at approximately the rate expected for a monomer (FIG. 2; compare lanes 1 and 5). Moreover, $SdG_4(T_4G_4)_3$, that displayed V3 binding similar to homopolymeric oligodeoxynucleotides, migrates predominately at the rate expected for a dimer. Although the 12-mer and 28-mer oligodeoxynucleotides containing the $-SdG_4-$ motif did not migrate with the characteristic retardation of tetraplexes, it was of interest that the migration of the 12-mer $SdG_4T_4G_4$ is somewhat slower than that of $SdC_{19}$ (FIG. 2; compare lanes 2 and 3). Moreover, the migration of the 28-mer $SdG_4(T_4G_4)_3$ is also slightly slower than that of $SdC_{28}$(FIG. 2; compare lanes 1 and 3). This slow migration is still observed even after treatment of the oligodeoxynucleotides with 10M urea/formamide (FIG. 2; compare lanes 2 [$SdC_{28}$] and 5 [$SdG_4(T_4G_4)_3$]). The reason for the relatively slow migration of phosphorothioate oligodeoxynucleotides containing the $-SdG_4-$motif is obscure.

Taken together, these data suggested that the tandem $-SdG_4$-repeats in $SdG_4T_4G_4$, in the absence of quadruple helix formation, increase the ability of the phosphorothioate oligodeoxynucleotides to bind to the V3 loop of gp120. Moreover, despite the presence of higher order structure in $SdG_4(T_4G_4)_3$, our data indicate that the augmentation of phosphorothioate oligodeoxynucleotides binding to gp120 V3 by $-SdG_4-$ motifs, while pronounced for smaller oligodeoxynucleotides (8- or 12-mers), is not significant for a phosphorothioate oligodeoxynucleotide of longer length (28-mer).

Discussion

In both solid phase ELISA assay and solution competition assay, the phosphorothioate oligodeoxynucleotides $SdT_2G_4T_2$ and $SdG_4T_4G_4$ demonstrate sequence-dependent augmentation of binding to the V3 loop of gp120 relative to other phosphorothioate oligodeoxynucleotides of similar length and base composition. The V3-loop binding data correlates with the relative abilities of these oligodeoxynucleotides to inhibit HIV-1 after cell-free or cell-associated infection of lymphocytoid H9 cells or of monocytoid U937 cells. Moreover, in each case, the potency of small oligodeoxynucleotides (8-12 mers) was enhanced by $-SdG_4-$ motifs, but this augmentation was not observed for longer oligodeoxynucleotides (e.g. 28-mers; $SdG_4(T_4G_4)_3$ or $SdC_{28}$ displayed similar V3 binding and inhibition of HIV-1 infectivity). Finally, examination of the solution structures of these oligodeoxynucleotides, studied by SDS gel electrophoresis, showed that $-S-dG_4-$ motifs augment the V3 binding and anti-HIV-1 effects of the 12-mer $SdG_4T_4G_4$ oligodeoxynucleotide in the absence of guadruple helix formation.

In both solid phase ELISA assay and solution competition assay, the phosphorothioate oligodeoxynucleotides $SdT_2G_4T_2$ and $SdG_4T_4G_4$ demonstrate sequence-dependent augmentation of binding to the V3 loop of gp120 relative to other oligodeoxynucleotides of similar length and base composition. In addition, the use of conventional polyacrylamide gels enables relatively facile determination of the nature of molecules formed by oligodeoxynucleotides folding [27]. However, whereas $SdT_2G_4T_2$ exists predominantly as a quadruple helix in polyacrylamide gels. $SdG_4T_4G_4$ has the appropriate gel mobility of a monomer. These data suggest that augmentation of V3 binding efficiency and the anti-HIV activity of these G-rich compounds are not solely dependent on the formation of higher order complexes [25, 26]. Rather, the presence of four contiguous guanosine residues alone is sufficient to increase activity. The ability of oligodeoxynucleotides with four contiguous guanosine residues to non-specifically bind with high affinity to proteins, such as basic fibroblast growth factor, has previously been noted [34].

The binding of deoxyguanosine containing phosphodiester oligodeoxynucleotides to the V3 loop is also of interest relative to whether the V3 loop has specific target structures on cells and if so, may provide insight into the chemical nature of the V3-target structure interaction. Several observations suggest that the V3 loop may have a molecular ligand or target. First, it is notable that although variable in primary sequence, the V3 loop of gp120 of all pathogenic strains of HIV-1 is positively charged and known to interact with sulfated polysaccharides [4-9]. On the V3 loop of the HIV-1 $_{111B}$ gp120 that binds mAb 9284, there are three arginine and one lysine residues in a 12 amino-acid epitope [18] indicating that the N-terminal region of the V3 loop that binds mAb 9284 contains a dense region of positive charges. These properties suggest that the molecular target(s) for V3 may be negatively charged moieties.

In this regard, the V3 has been shown to interact with cell surface sulfated proteoglycans (heparan sulfate [40]), sulfated glycolipids (3' sulfogalactosyl ceramide [39]). In addition, V3 interacts with proteinaceous species on U937 and Molt-4 cells [41], which might contain carbohydrate moieties, (for example sialyl-groups), since lectins are known to have clusters of positively charged amino acids at their carbohydrate-binding regions [38]. A separate line of inquiry has observed interactions between V3 and a cell surface protease, cathepsin G and has suggested that cathepsin G cleaves the V3 loop [35, 36]. The fact that V3 may interact with a variety of target structures is also supported by the finding that the V3 plays a role in restricting viral trophism for macrophages/neural cells or T cells [37, 22, 21] which may depend on interactions with cell-type specific cell surface molecules. Furthermore, it is probably the positively charged V3 region that is primarily responsible for the binding of phosphorothioate oligodeoxynucleotides.

The possibility exists that one or more ligands for the V3 loop will be identified and the phosphorothioate oligonucleotides described are expected to inhibit the interaction of the V3 loop with such structures. For example, recently a seven transmembrane domain protein, with homology to chemokine receptors, has been identified, termed fusin, that functions as a co-factor for human CD4 in allowing HIV-1 infection of mouse cells [44]. Since several members of the C—C and C-X-C chemokine receptor family have negatively charged motifs (characterized by E-rich stretches) in the ligand binding domains, it is possible that fusin and other related members of this family may bind the positively charged V3-loop of gp120. Thus, the phosphorothioate oligonucleotides described herein bind to the V3 loop and inhibit the interaction of the V3 loop with such co-receptors such as chemokine receptors.

Polyanions appear to have advantages over mAbs in interacting with the V3 loop, because these compounds bind to and inhibit the infectivity of a diverse range of viral isolates. In this regard, phosphorothioate oligodeoxynucleotides thus share several potentially important anti-HIV properties with sulfated polysaccharides, but may have some advantages. Oligodeoxynucleotides are discrete compounds and $SdC_{28}$ binds more avidly to gp120 than sulfated polysaccharides. Moreover, the potential utility of phosphorothioate oligodeoxynucleotides as therapeutic anti-HIV agents is further supported by their ability to inhibit HIV-1 infection in both lymphocytoid and monocytoid cell lines and by the fact that compounds such as $SdG_4T_4G_4$ and $SdG_4(T_4G_4)_3$ are not toxic to human cell lines in vitro.

These data are also interesting from the point of view of drug design. To the extent that small oligodeoxynucleotides are easier to manufacture, the 12-mer $SdG_4T_4T_4$ may be an important lead compound. On the other hand, the longer oligodeoxynucleotides represent a distinct class of lead compounds because they bind V3 potently. Since the binding of 28-mer is sequence insensitive to the best of our knowledge, it is possible that 28-mer sequences can be identified that confer other critical properties, such as augmentation of bioavailability. Furthermore, in addition to binding V3, phosphorothioate oligodeoxynucleotides bind to the gp120 binding site of CD4 [23], and may contribute to inhibition of infectivity, since, it is known that mAb binding to the V3 loop does not inhibit gp120-CD4 binding [23]. Thus, it is a goal of future research to determine if phosphorothioate oligodeoxynucleotides have synergistic effects on inhibiting HIV infectivity by inhibiting both the V3 function and gp120-CD4 binding. Together, these observations suggest that clinical therapeutic trials of 12-mer or 28-mer phosphorothioate oligodeoxynucleotides in patients at high risk for HIV-1 seroconversion (e.g., needle stick injuries) might well be worthwhile.

TABLE 1

Binding to gp120 V3 and inhibition of HIV-1 infectivity by phosphorothioate (PS) and phosphodiester (PO) oligodeoxynucleotides

| Abbrev. | OdX/PdX | V3 Binding $IC_{50}$ solid phase | gp120 Binding $K_d$ (nM) solution phase | H9 HIV inf. $IC_{50}$ (nM) | U937 HIV inf. $IC_{50}$ (nM) |
|---|---|---|---|---|---|
| $OdT_2G_4T_2$ | PO | >10,000 | 760,000 | N.D. | N.D. |
| $SdT_2G_4T_2$ | PS | 4,200 | 1,540 | 4,000 | 1,800 |
| $Od(TG)_4$ | PO | >10,000 | 10,200 | N.D. | N.D. |
| $Sd(TG)_4$ | PS | >10,000 | 900 | >10,000 | >10,000 |
| $OdG_4T_4G_4$ | PO | >10,000 | 4,650 | N.D. | N.D. |
| $SdG_4T_4G_4$ | PS | 160 | 50 | 550 | 550 |
| $SdG_4(T_4G_4)_3$ | PS | 42 | N.D. | 10 | N.D. |
| $SdC_{28}$ | PS | N.D. | *23 | 10 | N.D. |

*This data point was published previously in Stein, C. A., et al., Antisense Res. and Dev. 3: 19–31 (1993).

REFERENCES:

1. Schols, D., et al., Virology 175: 556–661 (1990).
2. Callahan, L. N., et al., J. Virol. 65: 1543–1550 (1991).
3. Lederman, S., et al., AIDS Res. Hum. Retroviruses 8: 1599–1610 (1992).
4. Ueno, R. and Kuno, S., Lancet 1: 1379 (1987).
5. Ito, M., et al., Antiviral Res. 7: 361–367 (1987).
6. Baba, M., et al., Antiviral Res. 9: 335–343 (1988).
7. Mitsuya, H., et al., Science 240: 646–649 (1988).
8. Schols, D., et al., J. Acquir. Immun. Defic. Syndr. 2: 10–15 (1989).
9. Schols, D., et al., Cytometry 11: 736–743 (1990).
10. Majumdar, C., et al., Biochemistry 28: 1340–1346 (1989).
11. Stein, C. A., et al., J. Acquir. Immun. Defic. Syndr. 4: 686–693 (1991).
12. Stein, C. A., et al., AIDS Res. Hum. Retroviruses 5: 639–646 (1989).
13. Stein, C. A., et al., Antisense Res. and Dev. 3: 19–31 (1993).
14. Wyatt, J. R., et al., Proc. Natl. Acad. Sci. U.S.A. 91: 1356–1360 (1994).
15. Williamson, J. R., Curr. Opin. Struct. Biol. 3: 357–362 (1993).
16. Williamson, J. R., Proc. Natl. Acad. Sci. U.S.A. 90: 3124 (1993).
17. Laughlan, G., et al., Science 265: 520–524 (1994).
18. Skinner, M. A., et al., AIDS Res. Hum. Retroviruses 4: 187–197 (1988).
19. Stein, C. A., et al., Nucleic. Acids. Res. 16: 3209–3221 (1988).
20. Matsushita, S., et al., J. Virol. 62: 2107–2114 (1988).
21. Hwang, S. S., et al., Science 253: 71–74 (1991).
22. Van den Berg, L. H., et. al., J. Neurosci. Res. 33: 513–518 (1992).
23. Skinner, M. A., et al., J. Virol. 62: 4195–4200 (1988).
24. Yakubov, L., et al., J. Biol. Chem. 268: 18818–18823 (1993).
25. Ojwang, J., et al., J. Acquired Imm. Def. Syndromes 7: 560–570 (1994).
26. Rando, R. F., et al., J. Biol. Chem. 270: 1754–1760 (1995).
27. Murchie, A. I., and Lilley, D. M., EMBO J. 13: 993–1001 (1994).
28. Harrop, H. A., et al., AIDS 8: 183–192 (1994).
29. Okada, T., et al., Biochem. & Biophys. Res. Comm. 209: 850–858 (1995).
30. Buckheit, R. W., et al., AIDS Res. & Hum. Retroviruses 10: 1497–1506 (1994).
31. Maniatis, T., et al., Molecular Cloning: A laboratory manual (Cold Spring Harbor, N.Y.: Cold Spring Harbor) (1982).
32. Cheng, Y. and Prusoff, W. H., Biochem. Pharmacol. 22: 3099–3108 (1973).
33. Prasad, V. R., et al., Proc. Natl. Acad. Sci. U.S.A. 88: 11363–11367 (1991).
34. Guvakova, M. A., et al., J. Biol. Chem. 270: 2620–2627 (1995).
35. Avril, L. E., et al., G. FEBS Letters 345: 81–86 (1994).
36. Avril, L. E., et al., FEBS Letters 367: 251–256 (1995).
37. Chavda, S. C., et al., J. Gen. Virol. 75: 32493253 (1994).
38. Drickamer, K., Curr. Opin. Struct. Biol. 3: 393400 (1996).
39. Harouse, J. M., et al., J. Virol. 69: 7383–7390 (1995).
40. Roderiquez, G., et al., J. Virol. 69: 2233–2239 (1995).
41. Xu, Y., et al., AIDS Res. Hum. Retroviruses 11: 563–570 (1995).
42. Skinner, M. A., et al., AIDS Res. Human Retroviruses 4(3): 187–197 (1988).
43. Goudsmit, J., AIDS 2: 157 (1988).
44. Feng, Yu, et al., Science 272: 872–876 (1996).
45. Rusche, James R., et al., Proc. Natl. Acad. Sci. U.S.A. (1988) 85: 3198–3202.
46. Ratner, et al., Nature (1985) 313: 277–284.

What is claimed is:

1. A phosphorothioate oligonucleotide moiety comprising a phosphorothioate oligonucleotide having the sequence $G_mX_nG_p$, wherein G is guanosine; X is thymidine or adenosine or a combination thereof; each of m, n and p is an integer from 3 to 10 inclusive; said phosphorothioate oligonucleotide moiety binding to a V3 loop of HIV envelope glycoprotein.

2. The phosphorothioate oligonucleotide moiety of claim 1, wherein X is thymidine or adenosine.

3. The phosphorothioate oligonucleotide moiety of claim 1, wherein each of m, n and p is 4 and X is thymidine.

4. The phosphorothioate oligonucleotide moiety of claim 1 which is stereo regular.

5. The phosphorothioate oligonucleotide moiety of claim 1 which is stereo non-regular.

6. The phosphorothioate oligonucleotide moiety of claim 1 which is stereo random.

7. The phosphorothioate oligonucleotide moiety of claim 1, wherein the phosphorothioate oligonucleotide is linked to a cholesteryl moiety.

8. The phosphorothioate oligonucleotide moiety of claim 1, wherein the phosphorothioate oligonucleotide is linked to an intercalating agent, a cross-linker, an artificial endonuclease, a lipophilic carrier, a peptide conjugate, or a combination thereof.

9. The phosphorothioate oligonucleotide moiety of claim 1, wherein the phosphorothioate oligonucleotide has a length of from about 8 to about 100 nucleotide residues.

10. The phosphorothioate oligonucleotide moiety of claim 1, wherein the phosphorothioate oligonucleotide is conjugated to a sulfated carbohydrate.

11. The phosphorothioate oligonucleotide moiety of claim 1, wherein the phosphorothioate oligonucleotide is conjugated to a carbohydrate or a glycan.

12. The phosphorothioate oligonucleotide moiety of claim 1, wherein the HIV envelope glycoprotein is HIV-1 gp120.

13. The phosphorothioate oligonucleotide moeity of claim 12, wherein the HIV envelope glycoprotein is the region of HIV-1 gp120 corresponding to C 302 to C 338 according to the standard numbering of HIV strain IIIb.

* * * * *